(12) United States Patent
Mertens et al.

(10) Patent No.: US 8,766,013 B2
(45) Date of Patent: Jul. 1, 2014

(54) METHOD FOR HYDROGENATION OF ISO-ALPHA-ACIDS AND TETRAHYDRO-ISO-ALPHA-ACIDS TO HEXAHYDRO-ISO-ALPHA-ACIDS

(75) Inventors: Pascal Mertens, Heverlee (BE); Dirk De Vos, Holsbeek (BE); Bart Steenackers, Kasterlee (BE)

(73) Assignee: Katholieke Universiteit Leuven (BE)

( * ) Notice: Subject to any disclaimer, the term of this patent is extended or adjusted under 35 U.S.C. 154(b) by 6 days.

(21) Appl. No.: 13/704,406

(22) PCT Filed: Jun. 14, 2011

(86) PCT No.: PCT/EP2011/059814
§ 371 (c)(1),
(2), (4) Date: Feb. 20, 2013

(87) PCT Pub. No.: WO2011/157692
PCT Pub. Date: Dec. 22, 2011

(65) Prior Publication Data
US 2013/0150626 A1 Jun. 13, 2013

(30) Foreign Application Priority Data
Jun. 14, 2010 (GB) .................................. 1009873.9

(51) Int. Cl.
*C07C 45/66* (2006.01)
(52) U.S. Cl.
USPC ............................ 568/341; 568/350; 568/379
(58) Field of Classification Search
CPC ............ C07C 51/36; C07C 45/66; C12C 3/12
USPC .................................................. 568/341, 350
See application file for complete search history.

(56) References Cited

U.S. PATENT DOCUMENTS

| 5,013,571 A | 5/1991 | Hay |
| 6,198,004 B1 | 3/2001 | Maye et al. |
| 7,344,746 B1 | 3/2008 | Wilson et al. |

FOREIGN PATENT DOCUMENTS

| DE | 19620171 A1 | 11/1997 |
| WO | 97/44304 | 11/1997 |
| WO | 2009/049381 A1 | 4/2009 |
| WO | 2010/068731 A1 | 6/2010 |

OTHER PUBLICATIONS

International Search Report, dated Sep. 22, 2011, issued in priority International Application No. PCT/EP2011/059814.
International Preliminary Report on Patentability, dated Jun. 6, 2012, issued in priority International Application No. PCT/EP2011/059814.

*Primary Examiner* — Sikarl Witherspoon
(74) *Attorney, Agent, or Firm* — Gianna Julian-Arnold; Saul Ewing LLP (57) ABSTRACT

The invention relates to a process for the production of hexahydro-iso-alpha-acids starting from iso-alpha-acids (or tetrahydro-iso-alpha-acids) in which iso-alpha-acids (or tetrahydro-iso-alpha-acids) are mixed with a heterogeneous ruthenium containing catalyst, that catalyzes the hydrogenation from iso-alpha-acids or tetrahydro-iso-alpha-acids to hexahydro-iso-alpha-acids, either in solvent-free conditions, or in the presence of a solvent phase (e.g. carbon dioxide, water, ethanol or another organic solvent, or mixtures thereof), and in the absence or presence of other hop compounds (such as beta-acids). The resulting mixture is then subjected to a temperature at which the iso-alpha-acid (or tetrahydro-iso-alpha-acid) containing reaction medium is sufficiently low in viscosity to allow easy mixing with the heterogeneous ruthenium containing catalyst and held under a hydrogen containing atmosphere (either pure hydrogen gas or mixed with an inert gas) for a reaction time sufficient to effect high conversion of the iso-alpha-acid (or tetrahydro-iso-alpha-acid) reactant into the hexahydro-iso-alpha-acid product.

22 Claims, 1 Drawing Sheet

METHOD FOR HYDROGENATION OF ISO-ALPHA-ACIDS AND TETRAHYDRO-ISO-ALPHA-ACIDS TO HEXAHYDRO-ISO-ALPHA-ACIDS

CROSS REFERENCE TO RELATED APPLICATIONS

This application claims the priority of PCT/EP2011/059814, filed on Jun. 14, 2011, which claims priority to Great Britain Application Nos. 1009873.9, filed Jun. 14, 2010, the entire contents of each of which are hereby incorporated in total by reference.

FIELD OF THE INVENTION

The present invention relates to the production of hexahydro-iso-alpha-acids (hexahydro-isohumulones or hexahydro-isohumulates) by the hydrogenation of iso-alpha-acids (iso-humulones or isohumulates) or tetrahydro-iso-alpha-acids (tetrahydro-isohumulones or tetrahydro-isohumulates) by using a heterogeneous ruthenium containing catalyst that catalyzes the hydrogenation from iso-alpha-acids or tetrahydro-iso-alpha-acids to hexahydro-iso-alpha-acids.

BACKGROUND OF THE INVENTION

The invention relates to the production of hexahydro-iso-alpha-acids, which are reduced derivatives of iso-alpha-acids, useful to impart bitterness and foam to beer. These hexahydro-iso-alpha-acids are bitter hop acid derivatives with excellent foam-stabilizing properties, and preferable to all other iso-alpha-acid products in terms of resistance to photolytic and oxidative degradation (U.S. Pat. No. 3,552,975).

Traditionally, the bitter beer flavor derives from the alpha-acids present in hop cones. During the wort boiling stage of the conventional brewing process, the alpha-acids are extracted from the (powdered) hop cones and partly converted to the corresponding bitter iso-alpha-acids. However, the hop utilization (or the iso-alpha-acid yield) in the traditional brewing process is only about 35% (GB 1,158,697).

It became clear that the hop utilization can be improved by performing the alpha-acid isomerisation outside the brewing process and more specifically by off-line pre-isomerising the alpha-acids under the effect of inorganic basic compounds (U.S. Pat. No. 3,962,061; U.S. Pat. No. 4,002,683; U.S. Pat. No. 4,758,445; U.S. Pat. No. 5,015,491; U.S. Pat. No. 5,155,276; U.S. Pat. No. 5,370,897). The use of such off-line produced iso-alpha-acids improves the utilization of the hop alpha-acids in the brewing process to about 70% at most.

The iso-alpha-acids have however a number of intrinsic disadvantages. One such negative property is their sensitivity to photolytic degradation which leads to the development of the so-called 'lightstruck flavor' which is ascribed to the formation of 3-methyl-2-butene-1-thiol (MBT), also called 'skunky thiol'. The occurrence of the photolytic reaction is a consequence of the presence of an iso-3-hexenoyl side chain in the iso-alpha-acid molecules. By modifying the molecular structure of the iso-alpha-acids, for example by reducing the C=C and/or C=O bonds in this iso-3-hexenoyl side chain, substantial MBT by-product formation, e.g. in beer, as a consequence of photolytic degradation can be prevented.

Consequently, reduced iso-alpha-acid derivatives have been introduced, to say dihydro-iso-alpha-acids, tetrahydro-iso-alpha-acids and hexahydro-iso-alpha-acids, and are now used by many brewers, generally by their addition after the primary fermentation stage of the brewing process. The dihydro-iso-alpha-acids (also called rho-iso-alpha-acids) are obtained by the reduction of the carbonyl group in the aforementioned iso-3-hexenoyl chain to a hydroxyl group, generally using alkali metal borohydride as the reducing agent. The tetrahydro-iso-alpha-acids are obtained via hydrogenation of the C=C bonds in the aforementioned iso-3-hexenoyl side chain and the isopentenyl side chain. The hexahydro-iso-alpha-acids are produced by combining the aforementioned reduction and hydrogenation processes.

All industrially applied procedures for the production of dihydro-iso-alpha-acids use a borohydride based reduction of iso-alpha-acids (U.S. Pat. No. 3,558,326; U.S. Pat. No. 4,324,810). The industrial processes for the production of tetrahydro-iso-alpha-acids generally apply heterogeneous Pd based catalysts (U.S. Pat. No. 5,013,571; U.S. Pat. No. 5,600,012).

For the formation of hexahydro-iso-alpha-acids two approaches have been described. The first type uses tetrahydro-iso-alpha-acids as the precursor and the desired hexahydro-iso-alpha-acids are obtained by a reduction using an alkali metal borohydride (U.S. Pat. No. 3,552,975). A second approach starts from dihydro-iso-alpha-acids, which are hydrogenated with hydrogen gas over a supported Pd catalyst (U.S. Pat. No. 5,013,571).

U.S. Pat. No. 3,552,975 describes the formation of the 'skunk-proof' hexahydro-iso-alpha-acids starting from tetrahydro-iso-alpha-acids, by using an alkali metal borohydride as the reducing agent, water and/or alcohol solvents as preferred inert protic reaction media, and mild alkaline pH conditions. After the reduction process, the excess reductant is decomposed by adding an aqueous HCl solution, and the hexahydro-iso-alpha-acids are recovered via extraction with a water-immiscible solvent (e.g. lower hydrocarbons or ethers). To obtain the hexahydro-iso-alpha-acid product in high purity, an additional solvent evaporation step is required.

U.S. Pat. No. 6,198,004 describes a process for converting iso-alpha-acids to tetrahydro-iso-alpha-acids by means of incremental or continuous addition to the reaction mixture of noble metal catalysts, preferably Pd catalysts, that catalyze the hydrogenation of the iso-alpha-acids towards tetrahydro-iso-alpha-acids, as supported by Pd catalyst based experimental data. However, U.S. Pat. No. 6,198,004 also teaches that when hexahydro-iso-alpha-acids are the desired products, the tetrahydro-iso-alpha-acid needs to be further reduced in a reduction step, that particularly employs a reducing agent of the alkali metal borohydride type.

U.S. Pat. No. 5,013,571 describes the reduction of iso-alpha-acids to dihydro-iso-alpha-acids with alkali metal borohydride compounds and the subsequent hydrogenation to hexahydro-iso-alpha-acids over Pd catalysts, with carbon, barium carbonate, barium sulphate, calcium carbonate or alumina as the supporting material. This patent also reflects the critical nature of these reduction and hydrogenation processes, by reporting side chain cleavage, during the reduction process as a consequence of the alkaline pH conditions, and during the hydrogenation process resulting from hydrogenolysis.

Approaches to avoid these perhydrogenation products are described in U.S. Pat. No. 5,600,012. If undesired side products resulting from hydrogenolytic degradation are present in the product, an additional extraction step using e.g. hexane is required to remove these degradation products followed by a solvent evaporation step to obtain the purified hexahydro-iso-alpha-acids.

U.S. Pat. No. 7,344,746 describes the production of hexahydro-iso-alpha-acids from dihydro-iso-alpha-acids via a (solvent-free) hydrogenation process using Pd and Pt based catalysts, with possible admixing of carbon dioxide, which can be performed in batch or continuous mode.

The above clearly shows that the transformation of hop iso-alpha-acids to hexahydro-iso-alpha-acids known in the art requires complex multistep processes, comprising hydrogenation and (alkali metal borohydride based) reduction reactions, with often the unwanted formation of degradation by-products (e.g. side chain cleavage and hydrogenolysis) that need to be removed by means of extraction and evaporation processes. Thus, there remains a need for improved, simplified methods to obtain hexahydro-iso-alpha-acids from iso-alpha-acids or tetrahydro-iso-alpha-acids.

SUMMARY OF THE INVENTION

The present invention relates to a method for the one-step production of hexahydro-iso-alpha-acids (hexahydro-isohumulones or hexahydro-isohumulates) using a heterogeneous ruthenium containing catalyst that catalyzes the hydrogenation of the iso-alpha-acid or the tetrahydro-iso-alpha-acid to the hexahydro-iso-alpha-acid, and to the hexahydro-iso-alpha-acid composition obtainable by said method.

Thus, a first aspect of the present invention provides a method for hydrogenating an iso-alpha-acid or a tetrahydro-iso-alpha-acid to a hexahydro-iso-alpha-acid comprising (i) contacting or mixing the iso-alpha-acid reactant (e.g. in the form of an iso-alpha-acid, an alkali metal isohumulate or an alkaline earth metal isohumulate) or the tetrahydro-iso-alpha-acid reactant (e.g. in the form of a tetrahydro-iso-alpha-acid, an alkali metal tetrahydro-isohumulate or an alkaline earth metal tetrahydro-isohumulate) with a heterogeneous ruthenium containing catalyst, that catalyzes the hydrogenation of said iso-alpha-acid or said tetrahydro-iso-alpha acid to the hexahydro-iso-alpha-acid, in the absence or in the presence of a solvent (such as carbon dioxide, water, ethanol or another organic solvent, or mixtures thereof) and in the absence or presence of other hop compounds (such as alpha acids or beta-acids), and (ii) holding this mixture under a hydrogen containing atmosphere. The hydrogen containing atmosphere may be obtained by pressurizing the reaction mixture with pure hydrogen or with hydrogen diluted with another gas, preferably an inert gas, such as nitrogen, helium, argon, carbon dioxide or a mixture thereof.

In contrast to what is known in the prior art, the method according to the present invention does not comprise an additional reduction reaction with an inorganic reducing agent to obtain hexahydro-iso-alpha-acids, such as an alkali metal borohydride based reducing agent (e.g. sodium or potassium borohydride) or an aluminium hydride based reducing agent (e.g. lithium aluminium hydride).

In a preferred embodiment of the present invention the hydrogenation reaction is carried out at a reaction temperature of at least 293 K, preferably in the range of 293 K to 398 K, more preferably between 333 K and 373 K, and most preferably between 343 K and 363 K. In another preferred embodiment the hydrogenation reaction is carried out using partial pressures of hydrogen varying between 0.02 MPa and 10.0 MPa, and more preferably between 0.1 MPa and 5.0 MPa, and most preferably between 0.2 MPa and 2.0 MPa.

The reaction time of the hydrogenation reaction is sufficient to achieve more than 99% conversion of the iso-alpha-acids (or the tetrahydro-iso-alpha-acids), both either in free acid form or in dissociated form (e.g. as in an isohumulate or a tetrahydro-isohumulate), with more than 90% selectivity to hexahydro-iso-alpha-acids (in free acid form or as a hexahydro-isohumulate).

The method according to the present invention may further comprise the step of isomerising an alpha-acid to said iso-alpha-acid (or a tetrahydro-alpha-acid to said tetrahydro-iso-alpha-acid) prior to or in the same reaction medium as the hydrogenation reaction.

The method according to the present invention may further comprise the step of separating the heterogeneous ruthenium containing catalyst from the obtained hexahydro-iso-alpha-acid product phase after the hydrogenation process, for instance by centrifugation, filtration, decantation or by another liquid-solid separation technique.

In a preferred embodiment of the present invention the heterogeneous ruthenium containing catalyst is a heterogeneous hydrogenation catalyst, comprising ruthenium on a supporting material, containing at least 0.1 weight % of ruthenium (based on total catalyst weight, including the supporting material) and at least 5 weight % of ruthenium on metals basis, with metals from the group of Ag, Au, Co, Cu, Ir, Ni, Pd, Pt, Rh and Ru. The supporting material of these Ru containing catalysts can be a carbon based material, an oxide or a hydroxide, a synthetic polymer, a biopolymer, a metallic structure, an organic-inorganic hybrid material, a zeolite, a clay or a salt material. Ruthenium is present in a metallic, hydroxide or oxide state. Preferably, the heterogeneous ruthenium containing catalyst is a ruthenium containing catalyst with carbon or alumina as the supporting material.

Next to ruthenium also one or more other (noble) metals e.g. Ag, Au, Co, Cu, Ir, Ni, Pd, Pt and Rh, can be part of the hydrogenation catalyst leading to hexahydro-iso-alpha-acids, and these (noble) metals can be present as a separate phase or a mixed phase with ruthenium or as an alloy. Also, the combination of a ruthenium containing catalyst together with another heterogeneous hydrogenation catalyst can be applied, for example the combination of Ru and Pd catalysts (with high and selective C=C hydrogenation activity). Ruthenium can be present in these hydrogenation catalysts in its metallic state or in a hydroxide or an oxide state.

Preferably, the mean particle size of the ruthenium fraction or ruthenium clusters present in the ruthenium containing catalysts is at least 1 nm and at most 1000 nm as measured by transmission electron microscopy.

In another preferred embodiment of the method of the present invention the molar ratio of the iso-alpha-acid or tetrahydro-iso-alpha-acid, either in free acid form or in dissociated form (as in isohumulates and tetrahydro-isohumulates), to the ruthenium fraction of the hydrogenation catalyst is between 1 and 2000, preferably between 10 and 500, more preferably between 20 and 200.

Another object of the present invention provides a hop hexahydro-iso-alpha-acid composition obtainable by the method according to the present invention. Particularly said hop hexahydro-iso-alpha-acid composition comprises at least 50, 60, 70 or 80 weight %, preferably at least 85 or 90 weight % hexahydro-iso-alpha-acids (based on total mass of alpha-acids, iso-alpha-acids and their hydrogenated and/or reduced derivatives), wherein said hexahydro-iso-alpha-acid composition is essentially free of inorganic compounds originating from an inorganic reducing agent, particularly a borohydride based reducing agent. Preferably, said hexahydro-iso-alpha-acid composition comprises less than 50 ppm of boron species as measured by elemental analysis. The hexahydro-iso-alpha-acid may be in its free acid form or in dissociated form. Said hop hexahydro-iso-alpha-acid composition may be solvent-free or the hexahydro-iso-alpha-acid may be dissolved in a suitable solvent.

DETAILED DESCRIPTION

List of Figures

Description

Surprisingly, the inventors found that the use of heterogeneous ruthenium containing catalysts allows a one-step reaction, more particularly a one-step hydrogenation, of hop iso-alpha-acids to hexahydro-iso-alpha-acids, without the need of a reduction step with an inorganic reducing agent, such as by using an alkali metal borohydride. Thus, the heterogeneous ruthenium containing catalyst is capable of catalyzing the hydrogenation of the C=C bonds of the iso-3-hexenoyl side chain and the isopentenyl side chain as well as the C=O bond of the iso-3-hexenoyl side chain. In contrast, the hydrogenation catalysts known in the art, such as the Pd containing catalysts, only catalyze the hydrogenation of the C=C bonds of the iso-3-hexenoyl side chain and the isopentenyl side chain. When using the hydrogenation catalysts known in the art (e.g. a Pd and Pt containing catalyst), the reduction of the C=O bond of the iso-3-hexenoyl side chain requires an additional reduction step using an inorganic reducing agent, such as sodium or potassium borohydride.

Figure 1:
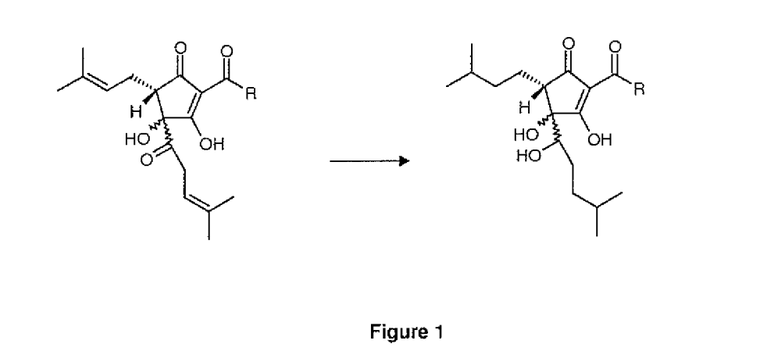
FIG. 1 shows the hydrogenation reaction of a hop iso-alpha-acid to a hexahydro-iso-alpha-acid, as catalyzed by the heterogeneous ruthenium containing catalysts, according to the present invention. In general, R is a lower alkyl, preferably a $C_1$-$C_6$ alkyl.
R=—$CH_2CH(CH_3)_2$: n-:
R=—$CH(CH_3)_2$: co-;
R=—$CH(CH_3)CH_2CH_3$: ad-;
R=—$CH_2CH_2CH(CH_3)_2$: pre-;
R=$CH_2CH_3$: post-.

The present invention provides an improved process for the conversion or hydrogenation of iso-alpha-acids to hexahydro-iso-alpha-acids using heterogeneous ruthenium containing catalysts, as schematically presented in FIG. 1. Thus, the present invention relates to a method for the hydrogenation of iso-alpha-acids comprising mixing an iso-alpha-acid containing feed and a heterogeneous ruthenium containing catalyst, in the presence of hydrogen gas (either pure or as a mixture with another gas), in the absence or in the presence of a suitable solvent, and in the absence or presence of other hop compounds (such as alpha-acids and beta-acids). Using the heterogeneous ruthenium containing catalysts and with alpha-acids and beta-acids in the process feed, the alpha-acids and beta-acids are hydrogenated to respectively tetrahydro-alpha-acids and hexahydro-beta-acids. The heterogeneous ruthenium containing catalyst is capable of catalyzing the hydrogenation of the C=C bonds in the isopentenyl side chains of the alpha-acids (with two isopentenyl side chains) and the beta-acids (with three isopentenyl side chains).

In the context of the present invention, the iso-alpha-acid containing feed is preferably a pre-isomerized alpha-acid extract, obtained by isomerisation of a hop extract, such as a hop alpha-acid enriched extract, with said hop extract preferably obtained by liquid or supercritical carbon dioxide extraction. In another embodiment of the present invention, the iso-alpha-acid containing feed can also be a mixture containing isohumulates or a solution of isohumulates (dissociated iso-alpha-acids), such as alkali metal isohumulates or alkaline earth metal isohumulates, in a solvent like water, carbon dioxide, organic solvents (including but not limited to methanol, ethanol, 1-propanol, 2-propanol or mixtures of those alcohol solvents) or mixtures thereof.

The invention also relates to a process for the hydrogenation of tetrahydro-iso-alpha-acids to hexahydro-iso-alpha-acids using heterogeneous ruthenium containing catalysts comprising mixing a tetrahydro-iso-alpha-acid containing feed (tetrahydro-iso-alpha-acids, in non-dissociated form or in dissociated form), and a heterogeneous ruthenium containing catalyst, in the presence of hydrogen gas (either pure or as a mixture with another gas), in the absence or in the presence of a suitable solvent, and in the absence or in the presence of other hop compounds (such as alpha-acids and beta-acids).

The invention also relates to a process for the substantially simultaneous isomerisation and hydrogenation of alpha-acids to hexahydro-iso-alpha-acids (and of tetrahydro-alpha-acids to hexahydro-iso-alpha-acids). By "substantially simultaneous" is meant that the isomerisation and hydrogenation occur in the same reaction medium, catalyzed by their respective catalysts, i.e. a suitable isomerisation catalyst and a heterogeneous ruthenium containing hydrogenation catalyst. Preferably, the process conditions are selected to assure that the isomerisation step precedes the hydrogenation reaction within the reaction medium. However, if the hydrogenation of the alpha-acids should occur prior to the alpha-acid isomerisation, this will result in the formation of predominantly tetrahydro-alpha-acids, which will next be isomerized to tetrahydro-iso-alpha-acids. Subsequently, these tetrahydro-iso-alpha-acids will be hydrogenated to hexahydro-iso-alpha-acids over the heterogeneous ruthenium containing catalyst according to the present invention. Suitable isomerisation catalysts for the isomerisation of hop alpha-acids are well known to the person skilled in the art. Preferably, said catalyst for the isomerisation of alpha-acids to iso-alpha-acids (or tetrahydro-alpha-acids to tetrahydro-iso-alpha-acids) is an alkaline earth metal based compound, acting as a heterogeneous catalyst, which essentially does not dissolve in the alpha-acid containing feed or in the (reduced) iso-alpha-acid product phase. More preferably said isomerisation catalyst is an alkaline earth metal based inorganic material of the aluminate, titanate, silicate or hydroxyapatite type, containing magnesium, calcium, strontium or barium or mixtures thereof.

In a preferred embodiment of the present invention, said method further comprises the step of holding the mixture under a hydrogen containing atmosphere, whereby said atmosphere is created by pressurizing the mixture using either pure hydrogen gas or hydrogen mixed with another gas, preferably an inert gas, such as nitrogen, argon, helium, carbon dioxide or a mixture thereof. Preferably, said reaction mixture is subjected in the presence of hydrogen gas to a temperature at which the iso-alpha-acid or tetrahydro-iso-alpha-acid containing reaction medium is sufficiently low in viscosity to allow easy mixing with the hydrogenation catalyst, preferably while stirring. Preferably, said temperature is at least 293 K. More preferably, the hydrogenation reaction is allowed to proceed for a time sufficient to achieve more than 95%, most preferably more than 99% conversion of the iso-alpha-acids (or tetrahydro-iso-alpha-acids) with more than 90% selectivity to hexahydro-iso-alpha-acids (in non-dissociated or in dissociated form, as for hexahydro-isohumulates). As understood by a person of ordinary skill in the art, the reaction time to obtain a >90% yield of hexahydro-iso-alpha-acids is, given a specific substrate to ruthenium ratio and for a specific iso-alpha-acid or tetrahydro-iso-alpha-acid containing process feed, dependent on the characteristics of the heterogeneous ruthenium containing catalyst, including but not limited to the mean particle size or the particle size distribution of the ruthenium clusters or the ruthenium fraction occurring in the ruthenium containing catalyst and the type of supporting material, and also dependent on the applied process conditions, such as reaction temperature and hydrogen pressure.

In the context of the present invention, the heterogeneous ruthenium containing catalysts are hydrogenation catalysts containing at least 0.1 weight % of ruthenium (on total mass of the catalyst, including supporting material) and at least 5 weight % of ruthenium on metals basis, with metals from the group of Ag, Au, Co, Cu, Ir, Ni, Pd, Pt, Rh and Ru. The supports of these ruthenium containing catalysts can be carbon based (e.g. carbon or activated carbon with varying pore and particle size, carbon nanotubes, graphene type materials), (hydr)oxides (e.g. single oxides or mixed oxides based on Mg, Ca, Sr, Ba, Al, Ti, Si), synthetic polymers (e.g. polyvinylpyrrolidone), biopolymers (e.g. chitosan), metallic structures (e.g. metal gauze), organic-inorganic hybrid materials (e.g. metallo-organic frameworks, coordination polymers etc.), zeolites (both of natural or synthetic origin), clays (e.g. bentonite) or salts (e.g. alkaline earth metal based carbonates, sulphates etc.). It is understood that this list is not limitative. With heterogeneous is meant that no significant or no substantial dissolution of ruthenium in the product phase can be measured by elemental analysis of the hexahydro-iso-alpha-acid product phase. More in particular, "no significant or no substantial dissolution of the ruthenium catalyst" is in the meaning that the product phase is essentially free of ruthenium. Preferably, less than 0.01%, more preferably less than 0.001% of the ruthenium present in the catalyst can be found in the hexahydro-iso-alpha-acid product phase, as measured by elemental analysis.

Next to ruthenium, also one or more other (noble) metals can be present, for example Ag, Au, Co, Cu, Ir, Ni, Pd, Pt and Rh. Again, it is understood that this list is not limitative. These additional (noble) metals can be present as a separate phase, or a mixed phase, or as an alloy with ruthenium. The ruthenium containing catalyst can also be combined with another heterogeneous hydrogenation catalyst based on the aforementioned (noble) metals. Ruthenium can be present in the ruthenium containing hydrogenation catalyst in its metallic state or as a hydroxide or an oxide. The ruthenium fraction or clusters present in the ruthenium containing hydrogenation catalyst (as they occur on the supporting material) have a particle size distribution varying between 1 nm and 1000 nm, preferably between 1.5 nm and 100 nm, more preferably between 2 nm and 25 nm, as determined by transmission electron microscopy.

The ruthenium containing hydrogenation catalyst can be used in a molar ratio of iso-alpha-acid (or the tetrahydro-iso-alpha-acid) to the ruthenium fraction of the hydrogenation catalyst varying between 1 and 2000, more preferably between 10 and 500, and most preferably 20 and 200.

In yet another embodiment of the present invention, the hydrogenation of iso-alpha-acids (or tetrahydro-iso-alpha-acids) to hexahydro-iso-alpha-acids catalyzed by a heterogeneous ruthenium containing catalysts occurs at moderate temperatures of at least 293 K. Preferably, the reaction mixture is kept at a reaction temperature in the range of 293 K to 398 K, and more preferably between 333 K and 373 K, most preferably between 343 K and 363 K. The reaction mixture is maintained at the preferred temperature for a reaction time which is in the range of 0.1 to 48 hours, more preferably in the range of 0.5 to 24 hours, most preferably in the range of 1 to 12 hours. During the hydrogenation reaction, an atmosphere containing hydrogen gas is maintained above the reaction mixture. Either pure hydrogen gas can be used or alternatively hydrogen gas mixed with another gas, particularly an inert gas like nitrogen, helium, argon, carbon dioxide or a mixture thereof. Partial pressures of hydrogen can vary between 0.02 and 10.0 MPa. More preferably the partial hydrogen pressure is in the range of 0.1 to 5.0 MPa, and most preferably between 0.2 and 2.0 MPa.

In another embodiment, organic molecules can be used as the hydrogen source in a process well known as transfer hydrogenation, as described in Heterogeneous Catalytic Transfer Hydrogenation and Its Relation to Other Methods for Reduction of Organic Compounds (R. A. W. Johnstone et al., Chemical Reviews 85 (1985) 129-170).

The heterogeneous ruthenium containing catalyst can be used in solvent-free conditions. Alternatively, water, carbon dioxide and organic solvents (e.g. methanol, ethanol, 1-propanol, 2-propanol or mixtures of those alcohol solvents) or a mixture thereof can be used as reaction medium.

Furthermore, the heterogeneous ruthenium containing catalyst can be separated from the reaction medium by means of simple centrifugation, filtration, decantation, or by other liquid-solid separation techniques thus allowing recycling of the catalyst.

The hydrogenation process can be conducted in a batch reactor whereby the ruthenium containing catalyst and the iso-alpha-acid (or tetrahydro-iso-alpha-acid) containing feed are loaded into the batch reactor at the beginning of the hydrogenation reaction. In another embodiment, the hydrogenation catalyst is used as a fixed bed in a tubular reactor and the iso-alpha-acid (or tetrahydro-iso-alpha-acid) containing feed is pumped through the reactor which allows the direct collection of the hexahydro-iso-alpha-acid product at the outlet of the reactor. Also other reactor and process designs that are generally known to people skilled in heterogeneous catalysis can be used. A non-limiting list of such reactor set-ups can be found in Applied Heterogeneous Catalysis (J.-F. Lepage et al., Institut Frçais du Pétrole, Editions Technip, 1987).

After high conversion of the iso-alpha-acid (or the tetrahydro-iso-alpha-acid) reactant in solvent-free conditions, the hexahydro-iso-alpha-acid product can be isolated as an organic liquid phase by any unit operation that is suitable for solid-liquid separations. Preferred techniques are centrifugation or filtration of the heterogeneous ruthenium containing catalyst, or decantation of the liquid layer. In case the hydrogenation reaction is performed in the presence of solvents, the solid-liquid separation allows to obtain solutions of the hexahydro-iso-alpha-acid product in water and/or organic solvents like ethanol. It is an advantage of the present invention, in the case of the solvent-free hydrogenation process, that no additional work-up operations are required, such as extraction and evaporation processes to obtain highly pure hexahydro-iso-alpha-acids as a product phase.

It is understood that the hydrogenation reaction according to the present invention is carried out without the need for an additional reduction step to obtain hexahydro-iso-alpha-acids, such as is the case in the methods to obtain hexahydro-iso-alpha-acids from iso-alpha-acids described in the prior art. Specifically, in the prior art hexahydro-iso-alpha-acids are obtained either (i) by alkali metal borohydride reduction of iso-alpha-acids to form dihydro-iso-alpha-acids, followed by (e.g. Pd catalyzed) hydrogenation of said dihydro-iso-alpha-acids to hexahydro-iso-alpha-acids or (ii) by (e.g. Pd catalyzed) hydrogenation of iso-alpha-acids to tetrahydro-iso-alpha-acids, followed by alkali metal borohydride reduction of said tetrahydro-iso-alpha-acids to form hexahydroiso-alpha-acids. Thus, it is an advantage of the present invention that the obtained hexahydro-iso-alpha-acids are essentially free of inorganic compounds originating from an inorganic reducing agent, such as borohydride or aluminium hydride based reducing agents. Particularly, the obtained hexahydro-iso-alpha-acids are essentially free of boron species originating from borohydride based reduction reactions.

Another object of the present invention provides a hexahydro-iso-alpha-acid composition, obtainable by the method according to the present invention without a reduction reaction with an inorganic reductant, such as alkali metal borohydride (e.g. sodium or potassium borohydride) or alkali metal aluminium hydride (e.g. lithium aluminium borohydride). Said hexahydro-iso-alpha-acid composition comprises at least 50, 60, 70, 80, 85 or 90 weight % hexahydro-iso-alpha-acids, expressed on total mass of alpha-acids, iso-alpha-acids and (hydrogenated and/or reduced) derivatives thereof, and is essentially free of inorganic compounds originating from an inorganic reducing agent. More preferably, said hexahydro-iso-alpha-acid composition is essentially free of boron species originating from borohydride based reduction reactions. More in particular, "essentially free of boron species" is in the meaning that said composition comprises less than 50, 40, 30, 20, 10 or 5 ppm boron as measured by elemental analysis.

The details of the invention will be explained below with reference to the Examples:

EXAMPLE 1

Solvent-Free Hydrogenation of Iso-Alpha-Acids with Ru/C Catalyst

All hydrogenation experiments were performed in triplicate for statistical reliability. The starting composition of the iso-alpha-acid reactant was >96% iso-alpha-acids; essentially no reduced iso-alpha-acids were present in the process feed, the alpha-acid content was <1 and the beta-acid content was <3%. 0.04 g of 5% Ru/C catalyst 0.02 mmol Ru), with a mean Ru particle size of 2 nm (as determined by transmission electron microscopy), was added to 0.36 g of iso-alpha-acid feed (≈1 mmol iso-alpha-acids). Next, the reaction mixture was stirred and heated to 333 K, 348 K or 363 K for varying reaction times. All reaction vessels were pressurized with 0.8 MPa hydrogen gas. After the hydrogenation reaction, the powder catalysts were separated from the reaction mixture by centrifugation.

The sample analyses were performed by means of an HPLC device equipped with a binary pump, vacuum degasser, autosampler, column thermostat, and diode array detector. Two Zorbax Extend C18 columns (150 mm length×4.6 mm inner diameter, packed with 5 μm particles) were used in series. The mobile phase consisted of 5 mM ammonium acetate in 20% (v/v) ethanol adjusted to a pH of 9.95 with ammonia (A solvent) and a mixture consisting of 60% acetonitrile (v/v) and 40% ethanol (v/v) (B solvent). The flow rate was set at 0.4 mL/min and solvent gradient elution was performed: 0-12 min: 0-16% B, 12-14 min: 16-25% B, 14-44 min: 25-40% B, 44-54 min: 40-60% B, 54-64 min: 60-90% B, 64-70 min: 90-100% B. The column temperature was maintained at 308 K. 100 μL volumes of filtered samples were injected. The UV detection was performed at 256 nm for the iso-alpha-acid reactants and the derived reduced iso-alpha-acid products, particularly dihydro-iso-alpha-acids, tetrahydro-iso-alpha-acids and hexahydro-iso-alpha-acids. The samples from the solvent-free hydrogenation experiments were analyzed after addition of 1 mL ethanol.

At a reaction temperature of 333 K, 0.36 g of iso-alpha-acids was converted with 0.04 g of 5% Ru/C catalyst (molar reactant:suthenium ratio=50) to hexahydro-iso-alpha-acids with a hexahydro-iso-alpha-acid yield of >90% alter 24 h (Table 1, entry 1). In the control experiment performed at 333 K without addition of the 5% Ru/C catalyst, <1% of the iso-alpha-acid reactant was converted after a 24 h reaction time (Table 1, entry 2). In an experiment identical to that of entry 1, but conducted for 20 h at 348 K, also a >90% hexahydro-iso-alpha-acid yield was obtained (Table 1, entry 3). At a reaction temperature of 363 K, the hexahydro-iso-alpha-acid yield was >90% after 16 h (Table 1, entry 5). The control experiments performed without the 5% Ru/C catalyst at 348 or 363 K did result in a <1% conversion of the iso-alpha-acid reactant (Table 1, entries 4 and 6).

Other Ru/C catalysts, with larger Ru particle sizes, were also evaluated. It was observed that 5% Ru/C catalysts characterized by larger mean Ru cluster particle sizes (3 nm-9 nm) required longer reaction times to obtain the >90% hexahydro-iso-alpha-acid yield level, but the same high selectivity to hexahydro-iso-alpha-acids was observed for these Ru catalysts.

It was also observed that, using the 5% Ru/C catalyst, the alpha-acids and beta-acids, present in low concentration in the iso-alpha-acid containing feed, were hydrogenated to respectively tetrahydro-alpha-acids and hexahydro-beta-acids.

TABLE 1

Solvent-free hydrogenation of iso-alpha-acids with Ru/C catalyst

| | reaction temperature | reaction time | catalyst | conversion of iso-alpha-acids | selectivity to hexahydro-iso-alpha-acids |
|---|---|---|---|---|---|
| entry 1 | 333 K | 24 h | 5% Ru/C | >99% | >90% |
| entry 2 | 333 K | 24 h | / | <1% | / |
| entry 3 | 348 K | 20 h | 5% Ru/C | >99% | >90% |
| entry 4 | 348 K | 20 h | / | <1% | / |
| entry 5 | 363 K | 16 h | 5% Ru/C | >99% | >90% |
| entry 6 | 363 K | 16 h | / | <1% | / |

Reaction conditions: molar reactant:ruthenium ratio = 50; 0.36 g reactant; 0.04 g catalyst.

EXAMPLE 2

Solvent-Free Hydrogenation of Iso-Alpha-Acids with Ru/Al$_2$O$_3$ Catalyst

The hydrogenation experiments were performed as described in Example 1, except for the type and amount of Ru containing catalyst. Here 0.08 g of 5% Ru/Al$_2$O$_3$, with a mean Ru particle size of 3 nm, was used instead of 0.04 g of 5% Ru/C applied in Example 1.

The sample analyses were performed as described in Example 1.

At a reaction temperature of 333 K, 0.36 g of iso-alpha-acids was converted with 0.08 g of 5% Ru/Al$_2$O$_3$ catalyst (molar reactant:ruthenium ratio=25) to hexahydro-iso-alpha-acids with a hexahydro-iso-alpha-acid yield of >90% after 24 h (Table 2, entry 1). Use of higher temperatures (348 K and 363 K instead of 333 K) allows shortening the reaction times required to achieve a >90% hexahydro-iso-alpha-acid yield, as described in entries 2 and 3 of Table 2.

It was observed that, using the 5% Ru/Al$_2$O$_3$ catalyst, the alpha-acids and beta-acids, present in low concentration in the process feed, were hydrogenated to respectively tetrahydro-alpha-acids and hexahydro-beta-acids.

TABLE 2

Solvent-free hydrogenation of iso-alpha-acids with Ru/Al$_2$O$_3$ catalyst

| | reaction temperature | reaction time | catalyst | conversion of iso-alpha-acids | selectivity to hexahydro-iso-alpha-acids |
|---|---|---|---|---|---|
| entry 1 | 333 K | 24 h | 5% Ru/Al$_2$O$_3$ | >99% | >90% |
| entry 2 | 348 K | 20 h | 5% Ru/Al$_2$O$_3$ | >99% | >90% |
| entry 3 | 363 K | 16 h | 5% Ru/Al$_2$O$_3$ | >99% | >90% |

Reaction conditions: molar reactant:ruthenium ratio = 25; 0.36 g reactant; 0.08 g catalyst.

EXAMPLE 3

Hydrogenation of Iso-Alpha-Acids in Water with Ru/C Catalyst

The starting composition of the iso-alpha-acid feed was 5 weight % iso-alpha-acids (present as potassium isohumulate salts) dissolved in water; essentially no reduced iso-alpha-acids were present in the process teed, the alpha-acid content was <1% and the beta-acid content was <1% on (alpha-acid+iso-alpha-acid+beta-acid) mass basis. 0.08 g of 5% Ru/C catalyst (≈0.04 mmol Ru) was added to 0.36 g of iso-alpha-acids (≈1 mmol iso-alpha-acids) dissolved in water. Next, the reaction mixture was stirred and heated to 333 K, 348 K or 363 K for varying reaction times. All reaction vessels were pressurized with 1.6 MPa hydrogen gas. After the hydrogenation reaction, the powder catalysts were separated from the reaction mixture by filtration using 5 μm filters.

The sample analyses were performed as described in Example 1, except for the sample post-treatment. The reaction samples were analyzed as such, without dilution in ethanol.

At a reaction temperature of 333 K, 0.36 g of iso-alpha-acids dissolved in water was converted with 0.08 g of 5% Ru/C catalyst (molar reactant:ruthenium ratio=25) to hexahydro-iso-alpha-acids with a hexahydro-iso-alpha-acid yield of >90% after 24 h (Table 3, entry 1). In experiments identical to that of entry 1, but carried out at temperatures of 348 K and 363 K, also a >90% hexahydro-iso-alpha-acid yield was obtained after respectively 20 h and 16 h (Table 3, entries 3 and 5). In the control experiments performed at 333 K, 348 K and 363 K without addition of the 5% Ru/C catalyst, <1% of the iso-alpha-acid reactant dissolved in water was converted (Table 3, entries 2, 4 and 6).

Hydrogenation processes analogous to entries 1, 3 and 5 of Table 3 were also performed with the 5% Ru/C catalyst pretreated by holding the catalyst under flowing hydrogen gas at 363 K for 1 h prior to application in the hydrogenation process. The catalytic performance of the pretreated 5% Ru/C catalyst was similar to that of the untreated Ru catalyst.

TABLE 3

Hydrogenation of iso-alpha-acids in water with Ru/C catalyst

| | reaction temperature | reaction time | catalyst | conversion of iso-alpha-acids | selectivity to hexahydro-iso-alpha-acids |
|---|---|---|---|---|---|
| entry 1 | 333 K | 24 h | 5% Ru/C | >99% | >90% |
| entry 2 | 333 K | 24 h | / | <1% | / |
| entry 3 | 348 K | 20 h | 5% Ru/C | >99% | >90% |
| entry 4 | 348 K | 20 h | / | <1% | / |
| entry 5 | 363 K | 16 h | 5% Ru/C | >99% | >90% |
| entry 6 | 363 K | 16 h | / | <1% | / |

Reaction conditions: molar reactant:ruthenium ratio = 25; 0.36 g reactant; 0.08 g catalyst.

EXAMPLE 4

Hydrogenation of Iso-Alpha-Acids in Water with Ru/Al$_2$O$_3$ Catalyst

The hydrogenation experiments and sample analyses were performed as described in Example 3, except for the type and amount of Ru catalyst. Here we use 0.16 g of 5% Ru/Al$_2$O$_3$.

At a reaction temperature of 333 K, 0.36 g of iso-alpha-acids dissolved in water was converted with 0.16 g of 5% Ru/Al$_2$O$_3$ catalyst (molar reactant:ruthenium ratio=12.5) to hexahydro-iso-alpha-acids with a hexahydro-iso-alpha-acid yield of >90% after 24 h (Table 4, entry 1). In analogous experiments performed at reaction temperatures of 348 K and 363 K, also a >90% hexahydro-iso-alpha-acid yield was obtained after respectively 20 h and 16 h (Table 4, entries 2 and 3).

TABLE 4

Hydrogenation of iso-alpha-acids in water with Ru/Al$_2$O$_3$ catalyst

| | reaction temperature | reaction time | catalyst | conversion of iso-alpha-acids | selectivity to hexahydro-iso-alpha-acids |
|---|---|---|---|---|---|
| entry 1 | 333 K | 24 h | 5% Ru/Al$_2$O$_3$ | >99% | >90% |
| entry 2 | 348 K | 20 h | 5% Ru/Al$_2$O$_3$ | >99% | >90% |
| entry 3 | 363 K | 16 h | 5% Ru/Al$_2$O$_3$ | >99% | >90% |

Reaction conditions: molar reactant:ruthenium ratio = 12.5; 0.36 g reactant; 0.16 g catalyst.

EXAMPLE 5

Hydrogenation of Iso-Alpha-Acids in Ethanol with Ru/C Catalyst

The starting composition of the iso-alpha-acid feed was 25 weight % iso-alpha-acids dissolved in ethanol; essentially no reduced iso-alpha-acids were present in the process feed, the alpha-acid content was <1% and the beta-acid content was <3% on (alpha-acid+iso-alpha-acid+beta-acid) mass basis. 0.04 g of 5% Ru/C catalyst (≈0.02 mmol Ru) was added to 0.36 g of iso-alpha-acids 1 mmol iso-alpha-acids) dissolved in ethanol. Next, the reaction mixture was stirred and heated to 333 K or 348 K for varying reaction times. All reaction vessels were pressurized with 2.0 MPa hydrogen gas. After the hydrogenation reaction, the powder catalysts were separated from the reaction mixture by centrifugation.

The sample analyses were performed as described in Example 1, except for the sample treatment prior to HPLC analysis. The reaction samples were analyzed as such, without further dilution in ethanol.

At 333 K, 0.36 g of iso-alpha-acids dissolved in ethanol was converted with 0.04 g of 5% Ru/C catalyst (molar reactant:ruthenium ratio=50) to hexahydro-iso-alpha-acids with a hexahydro-iso-alpha-acid yield of >90% after 28 h (Table 5, entry 1). In an experiment identical to that of entry 1, but performed at 348 K, a >90% hexahydro-iso-alpha-acid yield was obtained after respectively 24 h (Table 5, entry 3). In the control experiments performed at 333 K and 348 K without addition of the Ru/C catalyst, <1% of the iso-alpha-acid reactant was converted (Table 5, entries 2 and 4).

TABLE 5

Hydrogenation of iso-alpha-acids in ethanol with Ru/C catalyst

| | reaction temperature | reaction time | catalyst | conversion of iso-alpha-acids | selectivity to hexahydro-iso-alpha-acids |
|---|---|---|---|---|---|
| entry 1 | 333 K | 28 h | 5% Ru/C | >99% | >90% |
| entry 2 | 333 K | 28 h | / | <1% | / |
| entry 3 | 348 K | 24 h | 5% Ru/C | >99% | >90% |
| entry 4 | 348 K | 24 h | / | <1% | / |

Reaction conditions: molar reactant:ruthenium ratio = 50; 0.36 g reactant; 0.04 g catalyst.

EXAMPLE 6

Hydrogenation of Iso-Alpha-Acids in Ethanol Catalyst

The hydrogenation experiments and sample analyses were performed as described in Example 5, except for the type and amount of Ru containing catalyst. Here we use 0.08 g of 5% Ru/Al$_2$O$_3$.

At a reaction temperature of 333 K, 0.36 g of iso-alpha-acids dissolved in ethanol was converted with 0.08 g of 5% Ru/Al$_2$O$_3$ catalyst (molar reactant:ruthenium ratio=25) to hexahydro-iso-alpha-acids with a hexahydro-iso-alpha-acid yield of >90% after 28 h (Table 6, entry 1). In an analogous experiment conducted at a reaction temperature of 348 K, a >90% hexahydro-iso-alpha-acid yield was obtained after 24 h (Table 6, entry 2).

TABLE 6

Hydrogenation of iso-alpha-acids in ethanol with Ru/Al$_2$O$_3$ catalyst

| | reaction temperature | reaction time | catalyst | conversion of iso-alpha-acids | selectivity to hexahydro-iso-alpha-acids |
|---|---|---|---|---|---|
| entry 1 | 333 K | 28 h | 5% Ru/Al$_2$O$_3$ | >99% | >90% |
| entry 2 | 348 K | 24 h | 5% Ru/Al$_2$O$_3$ | >99% | >90% |

Reaction conditions: molar reactant:ruthenium ratio = 25; 0.36 g reactant; 0.08 g catalyst.

EXAMPLE 7

Solvent-Free Hydrogenation of Iso-Alpha-Acids with Ru/C and Pd/C Catalysts

The starting composition of the iso-alpha-acid reactant was >96% iso-alpha-acids; essentially no reduced iso-alpha-acids were present in the process feed, the alpha-acid content was <1% and the beta-acid content was <3%. 0.04 g of 5% Ru/C catalyst (≈0.02 mmol Ru) was added to 0.36 g of iso-alpha-acid feed (≈1 mmol iso-alpha-acids) for the Ru catalyzed iso-alpha-acid hydrogenation experiments. 0.04 g of 5% Pd/C (≈0.02 mmol Pd) was added to 0.36 g of iso-alpha-acid feed (≈1 mmol iso-alpha-acids) for the Pd catalyzed iso-alpha-acid hydrogenations. Next, the reaction mixture was stirred and heated to 348 K, for a reaction time of 20 h for the hydrogenation experiments with the Ru containing catalyst and for 16 h for the hydrogenation experiments with the Pd based catalyst. All reaction vessels were pressurized with 0.8 MPa hydrogen gas. After the hydrogenation reaction, the powder catalysts were separated from the reaction mixture by centrifugation.

The sample analyses were performed as described in Example 1.

TABLE 7

Solvent-free hydrogenation of iso-alpha-acids with Ru/C and Pd/C catalysts

| | reaction time | catalyst | conversion of iso-alpha-acids | selectivity to hexahydro-iso-alpha-acids |
|---|---|---|---|---|
| entry 1 | 20 h | 5% Ru/C | >99% | >90% |
| entry 2 | 16 h | 5% Pd/C | >99% | <1% |

Reaction conditions: molar reactant:ruthenium ratio = 50; molar reactant:palladium ratio = 50; 0.36 g reactant; 0.04 g catalyst; 348 K.

At a reaction temperature of 348 K, 0.36 g of iso-alpha-acids was converted with 0.04 g of the 5% Ru/C catalyst (molar reactant:ruthenium ratio=50) to hexahydro-iso-alpha-acids with a hexahydro-iso-alpha-acid yield of >90% after 20 h (Table 7, entry 1). At the same reaction temperature, the same amount of iso-alpha-acid reactants was converted with 0.04 g of the 5% Pd/C catalyst (molar reactant:palladium ratio=50) for >99% with a hexahydro-iso-alpha-acid yield below 1% and a tetrahydro-iso-alpha-acid yield exceeding 90% after 16 h (Table 7, entry 2).

EXAMPLE 8

Solvent-Free Hydrogenation of Iso-Aloha-Acids with a Combination of Ru/C and Pd/C Catalysts The starting composition of the iso-alpha-acid reactant was >96% iso-alpha-acids; essentially no reduced iso-alpha-acids were present in the process feed, the alpha-acid content was <1% and the beta-acid content was <3%. 0.04 g of 5% Ru/C (≈catalyst 0.02 mmol Ru) and 0.04 g of 5% Pd/C (≈0.02 mmol Pd) were added to 0.36 g of iso-alpha-acid feed (≈1 mmol iso-alpha-acids). Next, the reaction mixture was stirred and heated to 333 K, 348 K or 363 K for varying reaction times. All reaction vessels were pressurized with 0.8 MPa hydrogen gas. After the hydrogenation reaction, the powder catalysts were separated from the reaction mixture by centrifugation.

The sample analyses were performed as described in Example 1.

TABLE 8

Solvent-free hydrogenation of iso-alpha-acids with a combination of Ru/C and Pd/C catalysts

|  | reaction temperature | reaction time | catalyst | conversion of iso-alpha-acids | selectivity to hexahydro-iso-alpha-acids |
|---|---|---|---|---|---|
| entry 1 | 333 K | 16 h | 5% Ru/C + 5% Pd/C | >99% | >90% |
| entry 2 | 348 K | 12 h | 5% Ru/C + 5% Pd/C | >99% | >90% |
| entry 3 | 363 K | 8 h | 5% Ru/C + 5% Pd/C | >99% | >90% |

Reaction conditions: molar reactant:(ruthenium+palladium) ratio = 25; 0.36 g reactant; 0.04 g Ru/C catalyst + 0.04 g Pd/C catalyst.

At a reaction temperature of 333 K, 0.36 g of iso-alpha-acids was converted with 0.04 g of 5% Ru/C and 0.04 g of 5% Pd/C (molar reactant:(ruthenium+palladium) ratio=25) to hexahydro-iso-alpha-acids with a hexahydro-iso-alpha-acid yield of >90% after 16 h (Table 8, entry 1). In hydrogenation experiments identical to entry 1, but performed at 348 K and 363, also >90% hexahydro-iso-alpha-acid yields were obtained after respectively 12 h and 8 h (Table 8, entries 2 and 3).

EXAMPLE 9

Hydrogenation of Iso-Alpha-Acids, Dihydro-Iso-Alpha-Acids and Tetrahydro-Iso-Alpha-Acids in Water with Ru/C Catalyst The starting composition of the reactant was 5 weight % iso-alpha-acids, or 5 weight % dihydro-iso-alpha-acids, or 5 weight % tetrahydro-iso-alpha-acids (all present in the form of the derived potassium salts) dissolved in water; essentially no other (reduced) iso-alpha-acids than the intended reactants (respectively iso-alpha-acids, dihydro-iso-alpha-acids and tetrahydro-iso-alpha-acids) were present in the process feed, the alpha-acid content was <1% and the beta-acid content was 1% on (alpha-acid+(reduced) iso-alpha-acid+beta-acid) mass basis. 0.08 g of 5% Ru/C catalyst (≈0.04 mmol Ru) was added to 0.36 g of iso-alpha-acids (≈1 mmol iso-alpha-acids), or to 0.36 g of dihydro-iso-alpha-acids (≈1 mmol dihydro-iso-alpha-acids), or to 0.36 g of tetrahydro-iso-alpha-acids (≈1 mmol tetrahydro-iso-alpha-acids) dissolved in water. Next, the reaction mixture was stirred and heated to 348 K for varying reaction times. All reaction vessels were pressurized with 1.6 MPa hydrogen gas. After the hydrogenation reaction, the powder catalysts were separated from the reaction mixture by filtration.

The sample analyses were performed as described in Example 1, except for the sample post-treatment. The reaction samples were analyzed as such, without dilution in ethanol.

At a reaction temperature of 348 K, 0.36 g of iso-alpha-acids dissolved in water was converted with 0.08 g of 5% Ru/C catalyst (molar reactant:ruthenium ratio=25) to hexahydro-iso-alpha-acids with a hexahydro-iso-alpha-acid yield of >90% after 20 h (Table 9, entry 1). At a reaction temperature of 348 K, 0.36 g of dihydro-iso-alpha-acids dissolved in water was converted with 0.08 g of 5% Ru/C catalyst (molar reactant:ruthenium ratio=25) to hexahydro-iso-alpha-acids with a hexahydro-iso-alpha-acid yield of >90% after 12 h (entry 3). In the control experiment without the 5% Ru/C catalyst, <1% of the dihydro-iso-alpha-acid reactant was converted (entry 4). At a reaction temperature of 348 K, 0.36 g of tetrahydro-iso-alpha-acids dissolved in water was converted with 0.08 g of 5% Ru/C catalyst (molar reactant:ruthenium ratio=25) to hexahydro-iso-alpha-acids with a hexahydro-iso-alpha-acid yield of >90% after 16 h (entry 5). In the control experiment without the 5% Ru/C catalyst, <1% of the tetrahydro-iso-alpha-acid reactant was converted (entry 6).

Figure 2:
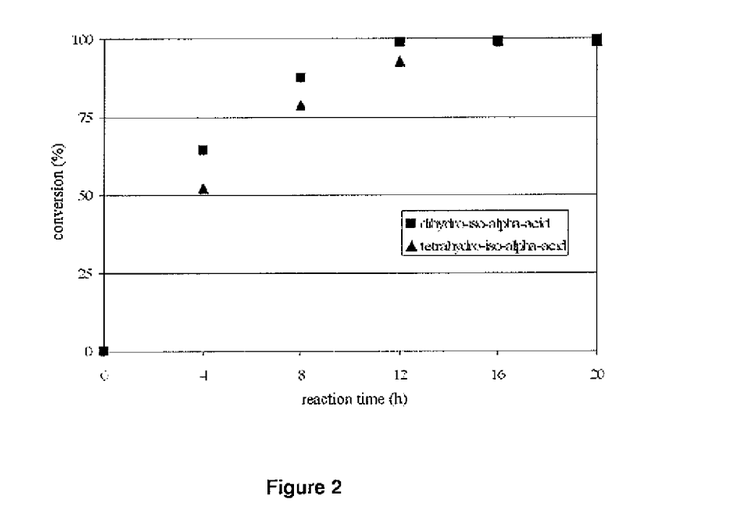
FIG. 2 shows the hydrogenation of dihydro-iso-alpha-acids and tetrahydro-iso-alpha-acids in water with Ru/C catalyst, particularly the time dependency of the reactant conversion.

The reaction time dependency of the conversion of the dihydro-iso-alpha-acids and tetrahydro-iso-alpha-acids, both leading to the hexahydro-iso-alpha-acid products, is reported in FIG. 2.

TABLE 9

Hydrogenation of iso-alpha-acids, dihydro-iso-alpha-acids and tetrahydro-iso-alpha-acids in water with Ru/C catalyst

|  | Reactant | reaction time | catalyst | conversion of reactant | selectivity to hexahydro-iso-alpha-acids |
|---|---|---|---|---|---|
| entry 1 | iso-alpha-acid | 20 h | 5% Ru/C | >99% | >90% |
| entry 2 | iso-alpha-acid | 20 h | / | <1% | / |
| entry 3 | dihydro-iso-alpha-acid | 12 h | 5% Ru/C | >99% | >90% |
| entry 4 | dihydro-iso-alpha-acid | 12 h | / | <1% | / |
| entry 5 | tetrahydro-iso-alpha-acid | 16 h | 5% Ru/C | >99% | >90% |
| entry 6 | tetrahydro-iso-alpha-acid | 16 h | / | <1% | / |

Reaction conditions: molar reactant:ruthenium ratio = 25; 0.36 g reactant; 0.08 g catalyst; 348 K.

EXAMPLE 10

Recycling of the Ru/C Catalyst in the Solvent-Free Hydrogenation of Iso-Alpha-Acids The hydrogenation experiments and sample analyses were performed as described in Example 1. After separation of the Ru/C catalyst powder from the reaction mixture by centrifugation, the Ru/C catalyst was reused in a next iso-alpha-acid hydrogenation.

At a reaction temperature of 333 K, 0.36 g of iso-alpha-acids was converted with 0.04 g of 5% Ru/C catalyst (molar reactant:ruthenium ratio=50) to hexahydro-iso-alpha-acids with a hexahydro-iso-alpha-acid yield of >90% after 24 h (Table 10, entry 1). At the same reaction temperature, 0.36 g of iso-alpha-acids was converted with 0.04 g of the recycled 5% Ru/C catalyst (molar reactant:ruthenium ratio=50) to hexahydro-iso-alpha-acids with a hexahydro-iso-alpha-acid yield of >90% after 24 h (Table 10, entry 2). Also in the case of higher reaction temperatures (348 K and 363 K), the performance of the 5% Ru/C catalyst proved stable upon recycling both in terms of hydrogenation activity and selectivity, as demonstrated in Table 10, entries 3 to 6.

TABLE 10

Recycling of the Ru/C catalyst in the solvent-free hydrogenation of iso-alpha-acids

|  | reaction temperature | reaction time | catalyst use | conversion of iso-alpha-acids | selectivity to hexahydro-iso-alpha-acids |
|---|---|---|---|---|---|
| entry 1 | 333 K | 24 h | no. 1 | >99% | >90% |
| entry 2 | 333 K | 24 h | no. 2 | >99% | >90% |
| entry 3 | 348 K | 20 h | no. 1 | >99% | >90% |

TABLE 10-continued

Recycling of the Ru/C catalyst in the solvent-free hydrogenation of iso-alpha-acids

| | reaction temperature | reaction time | catalyst use | conversion of iso-alpha-acids | selectivity to hexahydro-iso-alpha-acids |
|---|---|---|---|---|---|
| entry 4 | 348 K | 20 h | no. 2 | >99% | >90% |
| entry 5 | 363 K | 16 h | no. 1 | >99% | >90% |
| entry 6 | 363 K | 16 h | no. 2 | >99% | >90% |

Reaction conditions: molar reactant:ruthenium ratio = 50; 0.36 g reactant; 0.04 g 5% Ru/C catalyst.

EXAMPLE 11

Hydrogenation of Iso-Alpha-Acids with Ru/C Catalyst

Elemental Analysis on Reaction Products

The elemental analyses of the reaction samples were performed by means of an ICP-AES device. The spectral line used for the detection of Ru was 240.272 nm. Prior to elemental analysis of the reaction samples, a calibration curve was determined to relate the Ru concentration to the intensity of the detection signal. The samples from the solvent-free hydrogenation experiments, the hydrogenation experiments in water and the hydrogenation experiments in ethanol were analyzed after 100-fold dilution in water.

Under the conditions of the hydrogenation experiments in solvent-free conditions, in water medium and in ethanol medium, no leaching of Ru into the reaction medium was detected by ICP-AES from the Ru/C catalyst. In all cases, there was less than 0.01% of Ru dissolved from the 5% Ru/C catalyst into the product phase in the course of the hydrogenation experiments.

Other embodiments of the invention will be apparent to those skilled in the art from consideration of the specification and practice of the invention disclosed herein. It is intended that the specification and Examples be considered as exemplary only, with a true scope and spirit of the invention being indicated by the following claims:

The invention claimed is:

1. A process for hydrogenation of an iso-alpha-acid to a hexahydro-iso-alpha-acid comprising the steps of:
   (i) mixing an iso-alpha-acid containing feed with a heterogeneous ruthenium containing catalyst; and
   (ii) holding the mixture of the iso-alpha-acid containing feed and the heterogeneous ruthenium containing catalyst under an atmosphere comprising hydrogen to conduct the hydrogenation reaction,
   wherein the heterogeneous ruthenium containing catalyst catalyzes the hydrogenation of the iso-alpha-acid to the hexahydro-iso-alpha-acid.

2. The process according to claim 1, wherein said process does not comprise mixing the iso-alpha-acid containing feed with an inorganic reducing agent.

3. The process according to claim 1, wherein said iso-alpha-acid is in the free acid form or in dissociated form.

4. The process according to claim 1, further comprising the step of isomerising the alpha-acid to said iso-alpha-acid prior to or during the hydrogenation reaction.

5. The process according to claim 1, wherein said atmosphere comprising hydrogen is obtained by pressurizing said mixture with pure hydrogen or with hydrogen diluted with an inert gas selected from a group comprising at least one of nitrogen, helium, argon, carbon dioxide.

6. The process according to claim 1, wherein the hydrogenation reaction is conducted at a temperature of at least 293 K.

7. The process according to claim 6, wherein the hydrogenation reaction is carried out at a temperature between 333 K and 373 K.

8. The process according to claim 1, wherein the hydrogenation reaction is carried out under solvent-free conditions.

9. The process according to claim 1, wherein the hydrogenation reaction is carried out using a partial pressure of hydrogen in the range between 0.02 MPa and 10.0 MPa.

10. The process according to claim 1, further comprising the step of separating the heterogeneous ruthenium containing catalyst from a product mixture comprising the hexahydro-iso-alpha-acid obtained after the hydrogenation reaction, wherein the separating step comprises liquid-solid separation, and wherein the liquid-solid separation comprises at least one of centrifugation and filtration.

11. The process according to claim 1, wherein the heterogeneous ruthenium containing catalyst comprises at least 0.1 weight % of ruthenium on a supporting material, based on total catalyst weight, and at least 5 weight % of ruthenium on metals basis.

12. The process according to claim 11, wherein the supporting material of the ruthenium containing catalyst is selected from a group comprising carbon, an oxide, a hydroxide, a synthetic polymer, a biopolymer, a metallic structure, an organic-inorganic hybrid material, a zeolite, a clay material, and a salt material.

13. The process according to claim 11, wherein the ruthenium is present in a metallic, hydroxide or oxide state.

14. The process according to claim 11, wherein the ruthenium is present together with one or more other (noble) metals, wherein said metals are selected from the group consisting of Ag, Au, Co, Cu, Ir, Ni, Pd, Pt and Rh.

15. The process according to claim 14, wherein the ruthenium forms a separate phase from the other (noble) metal or metals.

16. The process according to claim 14, wherein the ruthenium forms a mixed or alloyed phase with the other (noble) metals.

17. The process according to claim 11, wherein the catalyst is ruthenium supported on carbon or ruthenium supported on alumina.

18. The process according to claim 11, wherein the ruthenium fraction as present in the catalyst has a mean particle size between 1 nm and 1000 nm.

19. The process according to claim 1, wherein the molar ratio of the iso-alpha-acid to the ruthenium is from about 1 to about 2000.

20. A process for hydrogenation of a tetrahydro-iso-alpha-acid to a hexahydro-iso-alpha-acid comprising the steps of:
   (i) mixing a tetrahydro-iso-alpha-acid containing feed with a heterogeneous ruthenium containing catalyst; and
   (ii) holding the mixture of the tetrahydro-iso-alpha-acid containing feed and the heterogeneous ruthenium containing catalyst under an atmosphere comprising hydrogen to conduct the hydrogenation reaction,
   wherein the heterogeneous ruthenium containing catalyst catalyzes the hydrogenation of the tetrahydro-iso-alpha-acid to the hexahydro-iso-alpha-acid.

21. The process according to claim 20, wherein said tetrahydro-iso-alpha-acid is in the free acid form or in dissociated form.

22. The process according to claim 20, further comprising the step of isomerising the tetrahydro-alpha-acid to the tetrahydro-iso-alpha-acid prior to or during the hydrogenation reaction.

* * * * *

UNITED STATES PATENT AND TRADEMARK OFFICE
CERTIFICATE OF CORRECTION

| | |
|---|---|
| PATENT NO. | : 8,766,013 B2 |
| APPLICATION NO. | : 13/704406 |
| DATED | : July 1, 2014 |
| INVENTOR(S) | : Pascal Mertens et al. |

Page 1 of 1

It is certified that error appears in the above-identified patent and that said Letters Patent is hereby corrected as shown below:

On the Title page, at item (73), Assignee name is:

IFAST NV

Signed and Sealed this
Thirteenth Day of October, 2015

Michelle K. Lee
*Director of the United States Patent and Trademark Office*